(12) United States Patent
Kamada

(10) Patent No.: US 9,364,166 B2
(45) Date of Patent: *Jun. 14, 2016

(54) MAGNETIC RESONANCE IMAGING APPARATUS AND BREATH-HOLDING IMAGING METHOD

(71) Applicant: Hitachi Medical Corporation, Tokyo (JP)

(72) Inventor: Yasuhiro Kamada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 232 days.

This patent is subject to a terminal disclaimer.

(21) Appl. No.: 14/087,027

(22) Filed: Nov. 22, 2013

(65) Prior Publication Data

US 2014/0081124 A1 Mar. 20, 2014

Related U.S. Application Data

(62) Division of application No. 13/122,309, filed as application No. PCT/JP2009/067213 on Oct. 2, 2009, now Pat. No. 8,618,800.

(30) Foreign Application Priority Data

Oct. 3, 2008 (JP) .................................. 2008-258535

(51) Int. Cl.
*A61B 5/055* (2006.01)
*G01R 33/565* (2006.01)
(Continued)

(52) U.S. Cl.
CPC .......... *A61B 5/055* (2013.01); *G01R 33/56509* (2013.01); *G01R 33/5602* (2013.01); *G01R 33/5607* (2013.01); *G01R 33/5613* (2013.01)

(58) Field of Classification Search
CPC .......... G01R 33/5602; G01R 33/5607; G01R 33/5613; G01R 33/56509; A61B 5/055
See application file for complete search history.

(56) References Cited

U.S. PATENT DOCUMENTS 5,590,654 A 1/1997 Prince
5,928,146 A 7/1999 Itagaki et al.
(Continued)

FOREIGN PATENT DOCUMENTS

EP 1139114 A2 10/2001
JP 7-178070 7/1995
(Continued)

OTHER PUBLICATIONS

R. B. Stafford, et al "Non-Contrast-Enhanced MRA of the Renal Vasculature with the bSSFP Dixon Method", Proc. Intl. Soc. Mag. Reson.Med. 16, May 3, 2008, p. 1379.

(Continued)

*Primary Examiner* — Dixomara Vargas
(74) *Attorney, Agent, or Firm* — Brundidge & Stanger, P.C.

(57) ABSTRACT

In order to make it possible to set the optimal breath-holding imaging conditions according to the subject without extension of an imaging time or the sacrifice of image quality, one scan is divided into one or more breath-holding measurements and free-breathing measurements on the basis of the imaging conditions of a breath-holding measurement, which are input and set according to the subject, and a region of the k space measured in the breath-holding measurement is controlled. Preferably, in the breath-holding measurement, low-frequency data of the k space is measured. Moreover, preferably, imaging conditions of the breath-holding measurement include the number of times of breath holding or a breath-holding time, and the operator can set any of these values.

17 Claims, 15 Drawing Sheets

(51) Int. Cl.
*G01R 33/56* (2006.01)
*G01R 33/561* (2006.01)

(56) References Cited

U.S. PATENT DOCUMENTS

| | | | |
|---|---|---|---|
| 6,198,959 | B1 | 3/2001 | Wang et al. |
| 6,397,097 | B1 | 5/2002 | Requardt |
| 6,434,413 | B1 | 8/2002 | Liu et al. |
| 6,611,701 | B2* | 8/2003 | Foo .............. G01R 33/5673 600/413 |
| 6,754,521 | B2 | 6/2004 | Prince |
| 6,957,097 | B2* | 10/2005 | Park .............. A61B 5/0263 600/410 |
| 8,078,259 | B2 | 12/2011 | Prince |
| 8,358,130 | B2* | 1/2013 | Stemmer ......... G01R 33/56375 324/307 |
| 8,461,837 | B2* | 6/2013 | Stemmer ......... G01R 33/56375 324/306 |
| 8,513,945 | B2* | 8/2013 | Kim .............. G01R 33/4818 324/309 |
| 8,618,800 | B2* | 12/2013 | Kamada .............. A61B 5/055 324/307 |
| 8,712,714 | B2* | 4/2014 | Horger .............. A61B 5/055 702/104 |
| 2011/0133735 | A1 | 6/2011 | Yokosawa et al. |
| 2011/0181286 | A1 | 7/2011 | Kamada |

FOREIGN PATENT DOCUMENTS

| | | |
|---|---|---|
| JP | 8-131418 | 5/1996 |
| JP | 2005040416 | 2/2005 |
| JP | 2007-29250 | 2/2007 |
| JP | 2007-75387 | 3/2007 |
| WO | 9846132 A1 | 10/1998 |
| WO | 2007/031916 | 3/2007 |

OTHER PUBLICATIONS

Y. L. Liu, et al, "MR Cardiac Imaging Using Breath-hold Gradient Echo Acquisition" Proceedings of the Computers in Cardiology Conference, London, Sep. 5, 1993, IEEE Comp. Soc. Press, US, vol. 5, Sep. 5, 1993, pp. 9-12.
P.A. Wielopolski, et al, Sequential 2D SSFP Volume Imaging of the Thorax, Proc. Intel. Soc.Mag.Reson.Med. 10, 2002, p. 404.
S. M. Shea, et al "3D Coronary Artery Imaging with Multiple Breath-Hods and Real-Time Adaptive Position Correction", Proc. Intl.Soc. Mag.Reson.Med.8, 2000, p. 262.
F. T. Johannes Arnold et al "Lung MRI using an MR-compatible active Breathing Control (MR-ABC)" Magentic Resonance in Medicine, vol. 58, No. 6, Jan. 1, 2007, pp. 1092-1098.
Jeffrey H. Maki et al, "The Effects of Incomplete Breath-Holding on 3D MR Image Quality", JMRI, vol. 7, Jan. 1, 1997, pp. 1132-1139.
Huber et al, Single Breath-Hold Extended Free-Breathing Navigator-Gated Three-Dimensional Coronary MRA, Journal of Magnetic Resonance Imaging, Feb. 2002, vol. 15, No. 2, pp. 210-214.
Amano et al, Fat-suppressed Three-dimensional MR Angiography Technique with Elliptical Centric View Order and No Prolonged Breath-holding Time, Proc. Intl. Soc. Mag. Reson. Med. 10, May 2002, #1756.
Pruessmann et al, SENSE: Sensitivity Encoding for Fast MRI, Magnetic Resonance in Medicine 42:952-962 (1999).
Weiger, et al, 2D SENSE for faster 3D MRI, Magnetic Resonance Materials in Physics, Biology and Medicine 14(2002) 10-19.

* cited by examiner (a) DESIGNATION OF BREATH-HOLDING TIME (b) DESIGNATION OF BREATH-HOLDING RATE (a) Scan#1

(b) Scan#2

(c) Scan#3

(a) Ky DIRECTION DIVISION (b) Kz DIRECTION DIVISION (c) Ky-Kz DIRECTION DIVISION (a) NORMAL SSFP MEASUREMENT (b-1) Scan#1    (b-2) Scan#2

(b) DIVIDED SSFP MEASUREMENT (a) NORMAL MULTI-ECHO MEASUREMENT (b) DIVIDED MULTI-ECHO MEASUREMENT

FIG. 12

| Scans | SIMULTANEOUS SETTING IN BREATH HOLDING |
|---|---|
| Scan T1W | ☑ |
| Scan T2W | ☑ |
| Scan T1WFS | ☑ |

1201

(a) SCAN SELECTION SCREEN

SIMULTANEOUS SETTING IN BREATH HOLDING

BH Time    12.0
BH Num.    1

1202
1203
1204

(b) SETTING SCREEN (a) SCREEN FOR DESIGNATING RATE OF CHANGE (b) SCREEN FOR SETTING BREATH-HOLDING TIME (a) Scan#1

(b) Scan#2

(c) Scan#3

MAGNETIC RESONANCE IMAGING APPARATUS AND BREATH-HOLDING IMAGING METHOD

CROSS-REFERENCED TO RELATED APPLICATIONS

The present application is a Divisional Application of application Ser. No. 13/122,309, filed Apr. 1, 2011; which is a 371 of PCT/JP2009/067213, filed Oct. 2, 2009; and claims priority of Japanese application No. 2008-258535, filed Oct. 3, 2008, the contents of which are incorporated herein by reference.

TECHNICAL FIELD

The present invention relates to breath-holding measurement in a nuclear magnetic resonance imaging (hereinafter, referred to as "MRI") apparatus which measures a nuclear magnetic resonance (hereinafter, referred to as "NMR") signal from hydrogen, phosphor, or the like in a subject and images nuclear density distribution, relaxation time distribution, or the like.

BACKGROUND OF THE INVENTION

The MRI apparatus is an apparatus which measures an NMR signal generated by the subject, especially, the nuclear spins which form human tissue and images the shapes or functions of the head, abdomen, limbs, and the like in a two-dimensional manner or in a three-dimensional manner. In the imaging, different phase encoding and different frequency encoding are given to NMR signals by the gradient magnetic field. Measured NMR signals are reconstructed as an image by two-dimensional or three-dimensional Fourier transform.

The measured NMR signals (hereinafter, referred to as echo signals) are digitized and arrayed as echo data in a k space (data space). In this case, if echo data with a change in the shape of the subject caused by breathing movement is arrayed in the same k space, motion artifacts appear on an image reconstructed from such k space data and lower the diagnostic performance. In order to reduce such motion artifacts, a respiratory gating method, a diaphragm navigator method, and a breath-holding method are used.

The respiratory gating method is a method of connecting a respiratory sensor to the subject to measure a breathing cycle and measuring the echo data only in a specific phase. For this reason, the echo data of the different respiratory phases is not mixed in the k space. As a result, motion artifacts can be reduced.

The diaphragm navigator method is a method of measuring the diaphragm position of the subject by measuring the echo data called navigator echoes and of measuring a breathing cycle from the position change. Although the method of measuring a navigator echo is the same as the respiratory gating method, it has a feature that a respiratory sensor is not necessary.

Finally, the breath-holding method is a method of making the subject stop breathing and measuring the echo data in the meantime. Thus, the breath-holding method is the simplest method because a respiratory sensor or acquisition of additional data is not required, and its clinical use is also widespread. Since one measurement needs to be performed within a time for which breath holding is possible in measurement using the breath-holding method, the breath-holding time is shortened by devising a sequence or a reconstruction method (parallel imaging or the like) in order to shorten the measurement time (Non-patent Documents 1 and 2).

Through combination of these known techniques, Patent Document 1 discloses a technique of repeatedly instructing the subject to perform breath holding and free breathing and performing imaging when body movement detected by a navigator echo after a breath-holding instruction falls within a predetermined range.

RELATED ART DOCUMENT

Patent Document

[PTL 1] JP-A-2007-29250

Non-Patent Document

[NPL 1] "SENSE: Sensitivity Encoding for Fast MRI", Magnetic Resonance in Medicine 42: 952-962 (1999)
[NPL 2] "2D SENSE for faster 3D MRI", Magnetic Resonance Materials in Physics, Biology and Medicine 14:10-19 (2002)

SUMMARY OF THE INVENTION

Technical Problem

Since a time for which breath holding is possible differs depending on a subject or the like, breath holding may not be maintained even in the optimized breath-holding conditions. As a result, motion artifacts may appear on the image. On the other hand, if a breath-holding time is simply shortened, the number of times of breath holding is increased and the total imaging time extends accordingly. As a result, the burden on the subject is increased. In the alternative, the breath-holding time or the number of times of breath holding should be reduced at the sacrifice of image quality, such as spatial resolution, time resolution, SNR, and CNR.

Therefore, it is an object of the present invention to make it possible to set the optimal imaging conditions of breath-holding measurement according to the subject without extension of the imaging time or the sacrifice of image quality.

Solution to Problem

In order to achieve the above-described object, an MRI apparatus and a breath-holding imaging method of the present invention divide one scan into one or more breath-holding measurements and free-breathing measurements on the basis of imaging conditions of breath-holding measurement, which are input and set according to the subject, and control a region of a k space measured in the breath-holding measurement.

Preferably, in the breath-holding measurement, data of low-frequency region of the k space is measured.

Moreover, preferably, imaging conditions of the breath-holding measurement include the number of times of breath holding or a breath-holding time, and the operator can set any of these values.

Advantageous Effects of Invention

According to the MRI apparatus and the breath-holding imaging method of the present invention, it is possible to set the optimal imaging conditions of breath-holding measurement according to the subject without extension of the imaging time or the sacrifice of image quality. As a result, even in the case of imaging of a part with body movement, it is possible to acquire a high-quality image without the sacrifice of image quality or an increase in the burden on the subject caused by extension of the imaging time.

BRIEF DESCRIPTION OF DRAWINGS

FIG. 12 is a view explaining a parameter setting screen used in the present invention.

DESCRIPTION OF PREFERRED EMBODIMENTS

Figure 1:
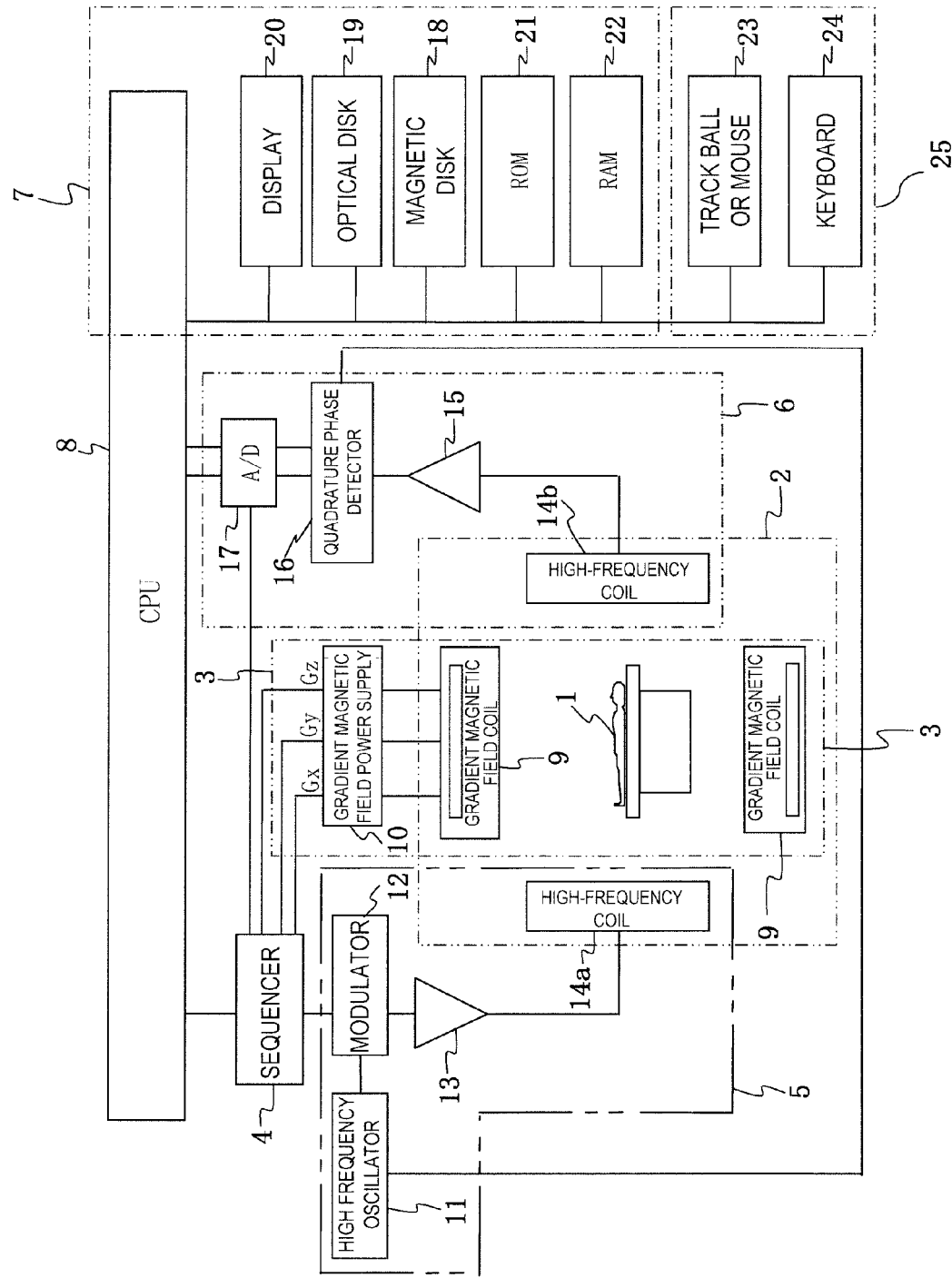
FIG. 1 is a perspective view of the entire basic constitution in an embodiment of an MRI apparatus related to the present invention.

Hereinafter, preferred embodiments of an MRI apparatus of the present invention will be described in detail according to the accompanying drawings. Moreover, in all drawings for explaining the embodiments of the invention, the same reference numeral is given to those with the same function and repeated explanation will be omitted.

First, the outline of an example of an MRI apparatus related to the present invention will be described on the basis of FIG. 1. FIG. 1 is a block diagram showing the overall configuration of an embodiment of the MRI apparatus related to the present invention. This MRI apparatus acquires a tomographic image of the subject using an NMR phenomenon. As shown in FIG. 1, the MRI apparatus is configured to include a static magnetic field generator 2, a gradient magnetic field generator 3, a signal transmitter 5, a signal receiver 6, an arithmetic processing section 7, and a measurement controller 4.

The static magnetic field generator 2 generates a uniform static magnetic field in the surrounding space of a subject 1 in a direction perpendicular to the body axis in the case of a vertical magnetic field method and in the body axis direction in the case of a horizontal magnetic field method. A permanent magnet type, a normal conducting type, or a superconducting type static magnetic field generator is disposed around the subject 1.

The gradient magnetic field generator 3 is formed by a gradient magnetic field coil 9 wound in three axial directions of X, Y, and Z, which are a coordinate system (stationary coordinate system) of the MRI apparatus, and a gradient magnetic field power supply 10 which drives each gradient magnetic field coil. The gradient magnetic field power supply 10 of each coil is driven according to a command from the measurement controller 4, which will be described later, so that the gradient magnetic fields Gx, Gy, and Gz in the three axial directions of X, Y, and Z are applied to a static magnetic field space where the subject 1 lies. At the time of imaging, a slice-direction gradient magnetic field pulse (Gs) is applied in a direction perpendicular to the slice surface (cross section of imaging) so that a slice surface of the subject 1 is set, and a phase-encoding-direction gradient magnetic field pulse (Gp) and a frequency-encoding-direction gradient magnetic field pulse (Gf) are applied in the two remaining directions, which are perpendicular to the slice surface and are also perpendicular to each other, so that the positional information in each direction is encoded in an echo signal.

The signal transmitter 5 irradiates a high-frequency magnetic field pulse (hereinafter, referred to as an "RF pulse") to the subject 1 in order to induce an NMR phenomenon in the nuclear spins of the atoms, which form the body tissue of the subject 1, and is configured to include a high frequency oscillator 11, a modulator 12, a high frequency amplifier 13, and a high-frequency coil (transmission coil) 14a at the transmission side. A high-frequency pulse output from the high frequency oscillator 11 is amplitude-modulated by the modulator 12 at a timing based on the command from the measurement controller 4, and the amplitude-modulated high-frequency pulse is amplified by the high frequency amplifier 13 and is then supplied to the high-frequency coil 14a disposed adjacent to the subject 1. As a result, an RF pulse is irradiated to the subject 1.

The signal receiver 6 detects an echo signal emitted by the NMR phenomenon of the nuclear spins, which form the body tissue of the subject 1, and is configured to include a high-frequency coil (receiving coil) 14b at the receiving side, a signal amplifier 15, a quadrature phase detector 16, and an A/D converter 17. An echo signal of a response of the subject 1 induced by the RF pulse irradiated from the high-frequency coil 14a at the transmission side is detected by the high-frequency coil 14b disposed adjacent to the subject 1 and amplified by the signal amplifier 15. Then, at a timing based on the command from the measurement controller 4, it is divided into two signals perpendicular to each other by the quadrature phase detector 16, and each of them is converted into a digital amount by the A/D converter 17 and transmitted to the arithmetic processing section 7 as echo data.

The arithmetic processing section 7 performs display, saving, and the like of various kinds of data processing and processing results and is configured to include a CPU 8, an external storage device such as an optical disk 19 or a magnetic disk 18, and a display 20. If echo data from the signal receiver 6 are input to the CPU 8, the echo data is stored in a memory corresponding to the K space in the CPU 8 (hereinafter, description of "arraying an echo signal or echo data in the K space" means that the echo data are written and stored in this memory. In addition, the echo data arrayed in the K space is called K space data). In addition, the CPU 8 executes arithmetic processing such as image reconstruction and signal processing on the K space data and displays a tomographic image of the subject 1, which is the result, on the display 20 and also records it in the external storage device.

The measurement controller 4 is a control means for repeating the application of an RF pulse and a gradient magnetic field pulse and the measurement of an echo signal on the basis of a certain predetermined pulse sequence, and it operates by control of the CPU 8 and transmits various commands, which are required to collect the echo data necessary for reconstruction of the tomographic image of the subject 1, to the gradient magnetic field generator 3, the signal transmitter 5, and the signal receiver 6.

An operating section 25 receives from an operator an input of various kinds of control information regarding the MRI apparatus or control information regarding the processing performed in the arithmetic processing section 7 and is configured to include a track ball or a mouse 23 and a keyboard 24. This operating section 25 is disposed adjacent to the display 20, so that the operator controls various kinds of processing of the MRI apparatus interactively through the operating section 25 while observing the display 20.

Moreover, in FIG. 1, the high-frequency coil 14a at the transmission side and the gradient magnetic field coil 9 are provided in the static magnetic field space of the static magnetic field generator 2, in which the subject 1 is inserted, such that they face the subject 1 in the case of a vertical magnetic field method and they surround the subject 1 in the case of a horizontal magnetic field method. In addition, the high-frequency coil 14b at the receiving side is provided so as to face or surround the subject 1.

Nuclides imaged by current MRI apparatuses, which are widely used clinically, are a hydrogen nucleus (proton) which is a main constituent material of the subject. The shapes or functions of the head, abdomen, limbs, and the like of the human body are imaged in a two-dimensional manner or in a three-dimensional manner by imaging of the spatial distribution of proton density or the information regarding the spatial distribution of a relaxation time of an excited state.

First Embodiment

Next, a first embodiment of the MRI apparatus and the breath-holding imaging method of the present invention will be described. In the present embodiment, corresponding to imaging conditions of breath-holding measurement which are input and set according to the subject, one scan is divided into one or more breath-holding measurements and free-breathing measurements and a region of the k space measured in the breath-holding measurement is controlled. Alternatively, one scan may be divided into only two or more breath-holding measurements with no free-breathing measurement. Preferably, low-frequency data of the k space is measured during the breath-holding measurement period. As imaging conditions for the breath-holding measurement, the number of times of breath holding and a breath-holding time are included.

Figure 2:
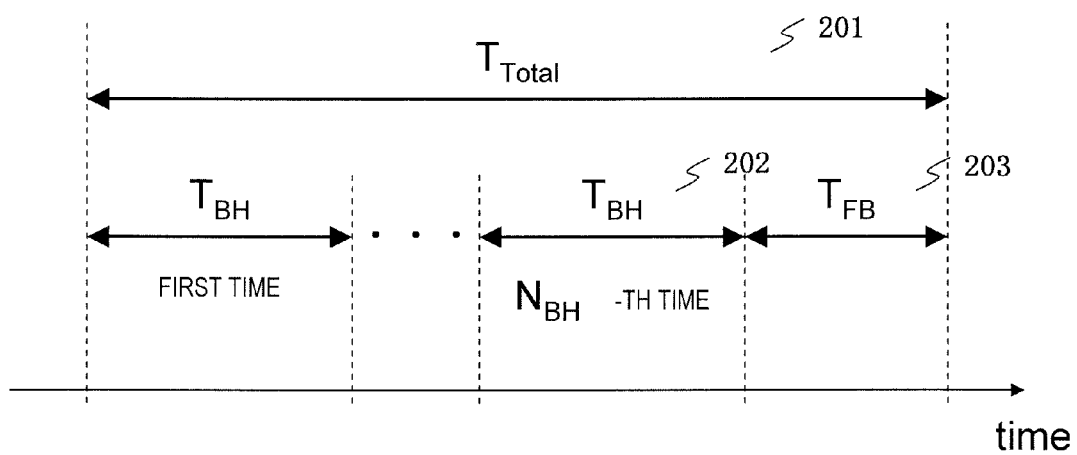
FIG. 2 is a view showing the processing concept of the present invention.
Figure 3:
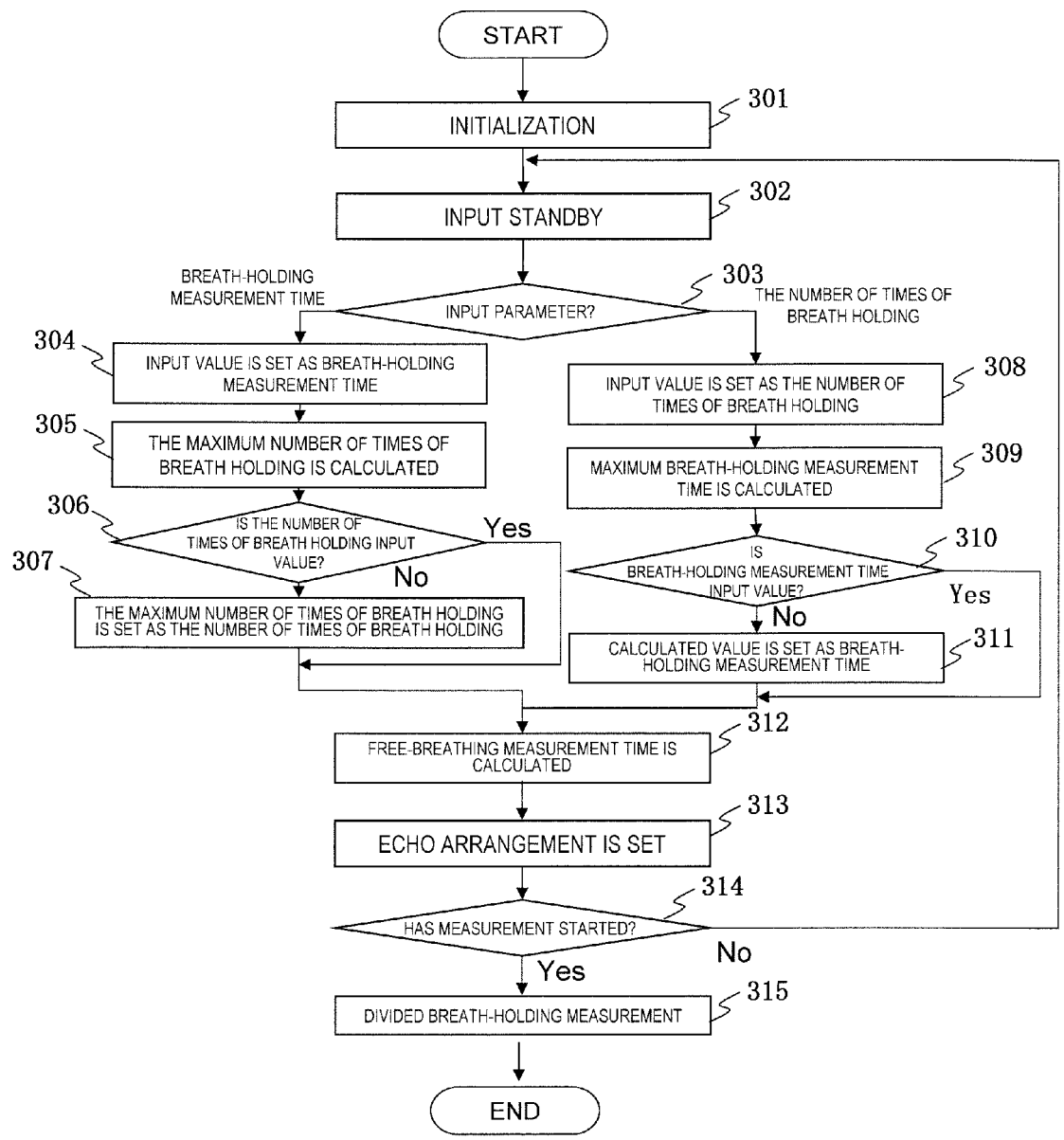
FIG. 3 is a view showing the process flow of the present invention.
Figure 4:
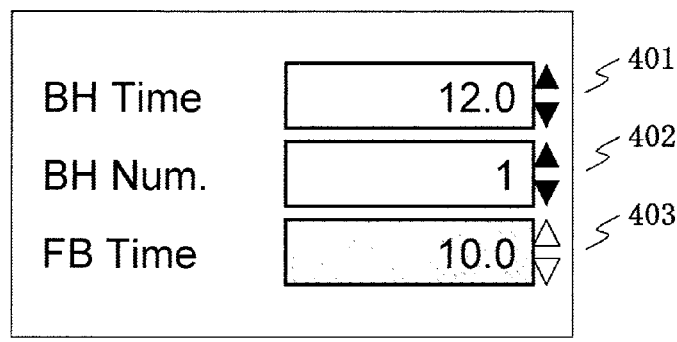
FIG. 4 is a view explaining a parameter setting screen used in the present invention.
Figure 4:
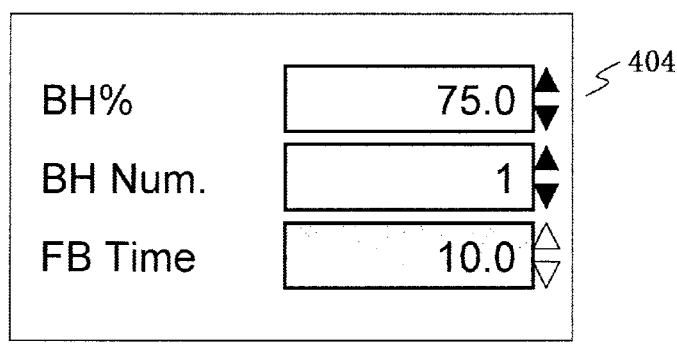
Figure 5:
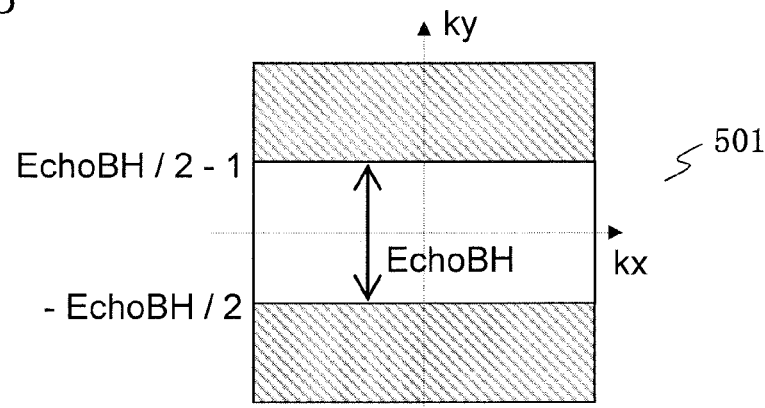
FIG. 5 is a view explaining a k space division method used in the present invention.
Figure 5:
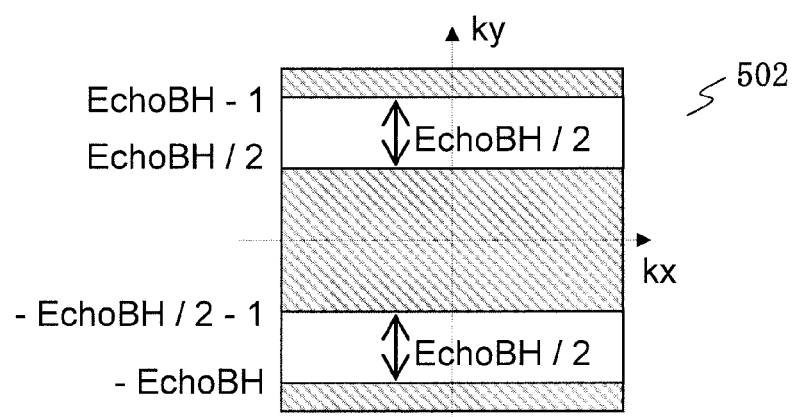
Figure 5:
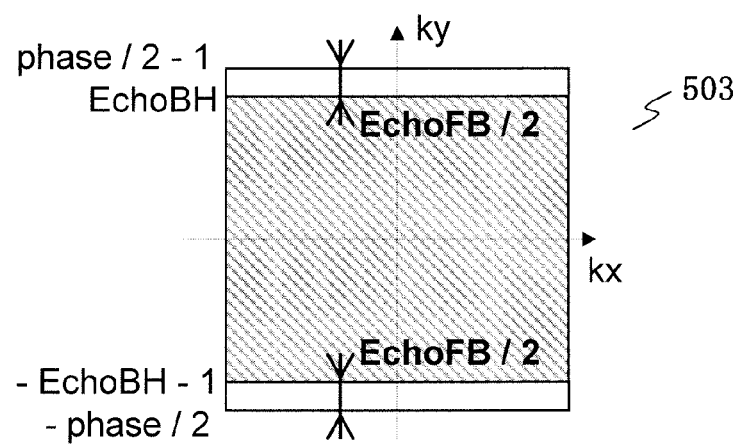

Hereinafter, the present embodiment will be described on the basis of FIGS. 2 to 4. FIG. 2 is a time chart showing the concept of the present embodiment, FIG. 3 is a flow chart showing an example of the process flow of the present embodiment, FIG. 4 is an example of an input section of the present embodiment, and FIG. 5 is an example of a processing result. In addition, in the present embodiment, a single scan is assumed in which a total measurement time TTotal [second] (201) is set.

$$TFB = TTotal - NBH \times TBH \qquad (1)$$

As shown in FIG. 2, in the present embodiment, one scan in which the total measurement time is TTotal is divided into NBH breath-holding measurements, free breathing is inserted between the breath-holding measurements, and free-breathing measurement is finally performed. In FIG. 2, each breath-holding period is set to the same TBH. However, each breath-holding period may be differently set. Therefore, in the present embodiment, a total of three parameters of breath-holding time TBH [second] (202), the number of times of breath-holding NBH [times] (202), and free-breathing measurement time TFB [second] (203) per scan are set. In addition, TFB is automatically decided from TTotal, TBH, and NBH on the basis of expression (1). As expressed by expression (1), a remaining time after performing "NBH" breath-holding measurements from the total measurement time is assigned to TFB. In addition, there are domains in TBH and TFB and they are 0≤TBH≤TTotal and 0≤TFB≤TTotal, respectively.

In subsequent explanations, when calculated values are substituted into TBH and TFB or when an operator sets a specific value through the operating section 25, it is rounded to 0 if the parameters become less than zero and to TTotal if the parameters exceed TTotal.

Hereinafter, a specific operation of the present embodiment will be described by explaining the processing of each step of the flow chart shown in FIG. 3 in detail. In addition, this process flow is stored in an external storage device as a program and is executed when the CPU 8 reads it into the memory to execute it as necessary.

$$TBH = TTotal$$
$$NBH = 1$$
$$TFB = 0 \qquad (2)$$

In step 301, first, the CPU 8 initializes each parameter by substituting the value shown in expression (2) into each parameter. In the initial state, it is normal breath-holding measurement in which a total measurement time is measured in one breath holding.

$$TBH = TTotal \times BH\% \qquad (3)$$

In step 302, the CPU 8 displays a GUI (graphical user interface) for setting of the parameters TBH and NBH on the display 20 so that input setting of the operator is possible and proceeds to an input standby state. An example of the GUI in this case is shown in FIG. 4. Here, BH Time (401), BH Num. (402), and FB Time (403) in FIG. 4(*a*) are set to TBH, NBH, and TFB as corresponding variable names, respectively. Since a remaining time after breath-holding measurement is assigned to TFB, it is not possible for a user to input TFB. A calculation result of expression (1) is displayed on FB Time of 403. In addition, as an alternative of a GUI which designates TBH of FIG. 4(*a*), it is also possible to use a GUI which designates a rate of breath holding BH % (404) in FIG. 4(*b*). Here, BH % is assumed to be a rate of one breath-holding time TBH in the total measurement time TTotal. That is, TBH and BH % can be converted to each other by the relationship of expression (3). Accordingly, if one of them is set, the other can be calculated.

Hereinafter, the case of setting TBH will be described.

In step 303, if input setting of TBH or the NBH is performed through the GUI in step 302, the CPU 8 proceeds to setting processing of another parameter.

First, processing (304 to 307) when TBH is input and set in step 302, which is a left branch of FIG. 3, will be described.

In step 304, if input setting of TBH is performed, the CPU 8 sets the input value as TBH as it is.

$$N_{BHMax} = \frac{T_{Total}}{T_{BH}} \qquad (4)$$

(round out anything below the decimal point)

In step 305, the CPU 8 calculates the maximum number of times NBHMax of breath holding from TBH set in step 304 on the basis of expression (4).

In step 306, the CPU 8 determines whether or not the set value of NBH is an input value of the operator in order to determine whether or not it is necessary to change NBH. If NBH is an automatically set value (No), the process proceeds to step 307. If NBH is input and set by the operator (Yes), step 307 is skipped to set the set value of the operator as it is without changing NBH. Then, the process proceeds to step 312.

In step 307, if NBH is an automatically set value, the CPU 8 sets NBHMax calculated in step 305 as NBH. Then, the process proceeds to step 312.

Next, processing (308 to 311) when there is input setting of NBH by an operator in step 302, which is a right branch of FIG. 3, will be described.

In step 308, if there is an input to NBH, the CPU 8 sets the input value as NBH as it is.

$$T_{BHMax} = \frac{T_{Total}}{N_{BH}} \quad (5)$$

In step 309, the CPU 8 calculates the maximum breath-holding time TBHMax from NBH set in step 308 on the basis of expression (5).

In step 310, the CPU 8 determines whether or not the set value of TBH is an input value of the operator in order to determine whether or not it is necessary to change TBH. In this case, if TBH is an automatically set value (No), the process proceeds to step 311. If TBH is input and set by the operator (Yes), step 311 is skipped to set the set value of the operator as it is without changing TBH. Then, the process proceeds to step 312.

In step 311, if TBH is an automatically set value, the CPU 8 sets TBHMax calculated in step 309 as TBH. Then, the process proceeds to step 312.

In step 312, the CPU 8 recalculates TFB using TBH and NBH changed by the above-described processing. Expression (1) is used to recalculate TFB.

In step 313, the CPU 8 sets the k space arrangement of echo data on the basis of the set three parameters. Details of the k space arrangement of echo data will be described later.

In step S314, the CPU 8 starts divided breath-holding measurements by the three parameters set up to step 312 and the k space arrangement of echo data set in step S313 or displays a measurement start button or the like on the display 20 in order to wait for the operator's determination. Before the operator starts measurement by pressing a measurement start button, the operator can reset the parameters. If a certain parameter is reset, the CPU 8 executes a corresponding step in each step described above.

If the measurement start button displayed in step 314 is pressed by the operator in step 315, the CPU 8 instructs the measurement controller 4 to start divided breath-holding measurements based on each parameter set as described above. In response to the instruction, the measurement controller 4 starts divided breath-holding imaging. Details of the measurement control will be described later.

Figure 14:
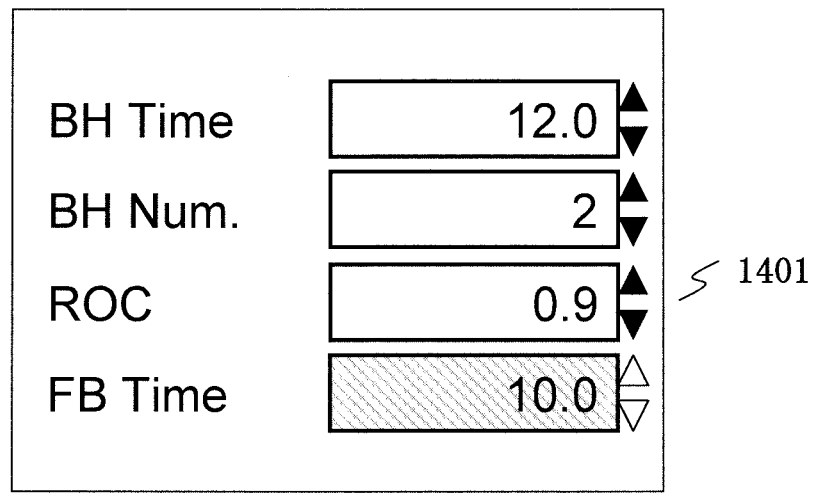
FIG. 14 is a view explaining a parameter setting screen used in the present invention.
Figure 14:
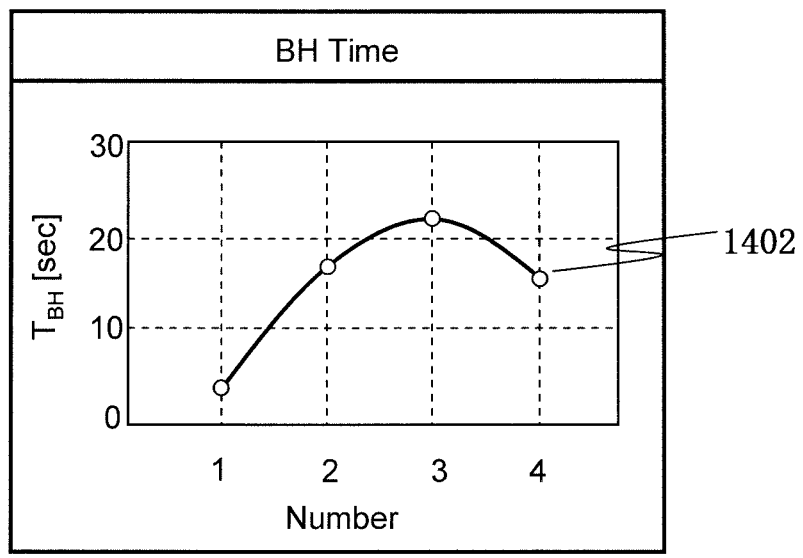

This is an explanation regarding the outline of an example of the process flow of the present embodiment. Moreover, in the above explanation, an example was described in which the number of times of breath holding and a breath-holding time were input and set as imaging conditions for breath-holding measurement. However, it is also possible to set one of them to a fixed value and to input and set only the other one. Moreover, in the above explanation, an example where there was free-breathing measurement was described. However, it is also possible to divide one scan into only two or more breath-holding measurements with no free-breathing measurement. Moreover, in the above explanation, every breath-holding time TBH was the same. However, if breath holding is repeated NBH times, a breath-holding possible time may be shorted by fatigue or fear of the subject as the number of times of breath holding n (1≤n≤NBH) increases. For this reason, as shown in FIG. 14, a breath-holding time may be changed according to the number of times of breath holding n using the rate of change ROC (Rate Of Change) (1401). Examples using the ROC are given in expressions (23a) and (23b).

$$TBHMod[n] = ROC^{n-1} \cdot TBH \quad (23a)$$

$$TBHMod[n] = (ROC - 1)(n - 1) \cdot TBH + TBH \quad (23b)$$
$$= \{(ROC - 1)(n - 1) + 1\} \cdot TBH$$

Here, TBHMod[n] indicates an n-th breath-holding time. In this case, if ROC=1.0 is assumed, it is preferable to use a function in which all breath holding of NBH times becomes fixed at TBH.

If ROC<1, the breath-holding time becomes short as breath holding progresses. If ROC>1, it is the opposite.

In addition, since the subject is unfamiliar with breath-holding measurement immediately after the start of examination, the breath-holding time may be shortened several times immediately after the start. In this case, the user may set the shape of TBHMod [n] freely by operating a graph or the like showing a breath-holding time of each breath holding which is displayed on the GUI (1402).

(k space arrangement setting of echo data; in the case of two dimension)

$$EchoBH = \frac{T_{BH}}{T_{Total}} \times \text{phase} \quad (6)$$
$$= \frac{T_{BH}}{N_{BH} \times T_{BH} + T_{F_B}} \times \text{phase}$$

Next, k space arrangement setting of echo data in step 313 will be described in detail. First, an example of two-dimensional measurement is shown in FIG. 5. In the present embodiment, one scan is divided into "NBH" breath-holding measurements and one free-breathing measurement and the echo data measured during the breath-holding period is preferentially arrayed in a low-frequency region of the k space. Therefore, in processing of step 313, first, the CPU 8 performs (NBH+1) division of the k space in the phase encoding direction. Here, assuming that the number of phase encoding measured during one scan is "phase", the number of echo data EchoBH which can be measured in one breath-holding measurement is expressed as expression (6).

$$-\frac{EchoBH}{2} \times n \leq ky \leq -\frac{EchoBH}{2} \times (n-1) - 1, \quad (7)$$
$$\frac{EchoBH}{2} \times (n-1) \leq ky \leq \frac{EchoBH}{2} \times n - 1$$

In addition, the range in a measurement direction (phase encoding direction) in n-th breath-holding measurement (1≤n≤NBH) can be expressed as expression (7) using EchoBH.

That is, data of a negative side region (first expression of (7)) and a positive side region (second expression of (7)) in the phase encoding direction with the origin of the k space interposed therebetween is measured. In the ky range set by expression (7), echo data is measured using the measurement order that the operator has designated on the GUI, similar to measurement in which the present invention is not applied. However, particularly in the case of measurement using breath holding and electrocardiographic synchronization together, the heart rate may be changed under the influence of breath holding at the start and end of measurement. Therefore, in the measurement in which the present invention is applied, a centric order in which the echo data is forcibly filled from the middle or the k space toward a high-frequency region immediately after the start of measurement may be used in consideration of a change in the heart rate caused by breath holding.

Moreover, in the case of a plurality of breath-holding measurements (NBH≥2), it is also possible to calculate a breath-holding position from the information including diaphragm navigation and to correct a slice position so that positional deviation between breath-holding measurements does not occur. A technique of eliminating such positional deviation between measurements is known in JP-T-9-508050 and the like.

$$EchoFB = \frac{T_{FB}}{T_{Total}} \times \text{phase} \qquad (8)$$
$$= \frac{T_{FB}}{N_{BH} \times T_{BH} + T_{FB}} \times \text{phase}$$
$$= \text{phase} - N_{BH} \times EchoBH$$

On the other hand, the number of echo data EchoFB measured in free-breathing measurement can be expressed as expression (8).

$$-\frac{\text{phase}}{2} \leq ky \leq -\frac{EchoBH}{2} \times N_{BH} - 1, \qquad (9)$$
$$\frac{EchoBH}{2} \times N_{BH} \leq ky \leq \frac{\text{phase}}{2} - 1$$

In addition, the ky range measured in the free-breathing measurement can be expressed as expression (9).

In the present embodiment, echo data is measured in order from the k space center toward a high-frequency region. However, the measurement order may be changed as long as the principle is followed in which echo data measured during a breath-holding period is arrayed at the middle side of the k space and echo data measured during a free-breathing period is arrayed at the high-frequency region side of the k space.

Moreover, in the present embodiment, as expressed by expression (9), the spatial resolution can be ensured even if a breath-holding time is shortened by arraying the echo data measured during the free-breathing period in a high-frequency region of the k space. Moreover, in this case, the order of encoding may be set at random so that motion artifacts resulting from breathing are not imaged on a specific position.

$$-\frac{EchoBH}{2} \leq ky \leq \frac{EchoBH}{2} - 1 \qquad (10)$$

In the above-described processing, a specific example of an arrangement of echo data into the k space when NBH=2 is assumed is shown in FIG. 5. Two breath-holding measurements are defined as Scan #1 and Scan #2, and one free-breathing measurement is defined as Scan #3. The phase encoding range measured in the first breath-holding measurement Scan #1 can be expressed as expression (10) by substituting n=1 into expression (7) (501).

$$-EchoBH \leq ky \leq -\frac{EchoBH}{2} - 1 \qquad (11)$$
$$\frac{EchoBH}{2} \leq ky \leq EchoBH - 1$$

The phase encoding range measured in the second breath-holding measurement Scan #2 can be expressed as expression (11) by substituting n=2 into expression (7) (502).

$$-\frac{\text{phase}}{2} \leq ky \leq -EchoBH - 1 \qquad (12)$$
$$EchoBH \leq ky \leq \frac{\text{phase}}{2} - 1$$

In addition, the phase encoding range measured in the free-breathing measurement Scan #3 can be expressed as expression (12) by substituting NBH=2 into expression (9) (503).

In this case, a level difference may occur in echo data at the boundary between divided regions of the divided k space. Such a level difference causes ringing artifacts in a reconstructed image. For this reason, it is also possible to add processing of reducing the level difference by increasing the number of echo data measured in each Scan so that the echo data of both sides overlap each other near the boundary between divided regions.

(k space arrangement setting of echo data; in the case of three dimension)

$$EchoBH = \frac{T_{BH}}{T_{Total}} \times \text{phase} \times \text{slice} \qquad (13)$$
$$= \frac{T_{BH}}{N_{BH} \times T_{BH} + T_{FB}} \times \text{phase} \times \text{slice}$$

Next, an example of three-dimensional measurement is shown. Here, assuming that the number of slice encoding is "slice", the number of echo data measured during one scan becomes "phase×slice". The number of echo data EchoBH which can be measured in one breath-holding measurement can be expressed as expression (13).

Figure 6:
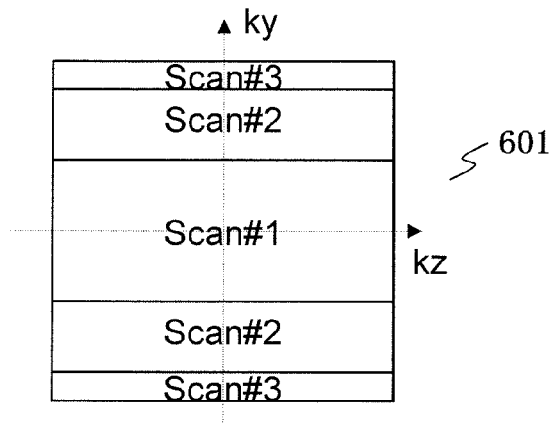
FIG. 6 is a view explaining a k space division method used in the present invention.
Figure 6:
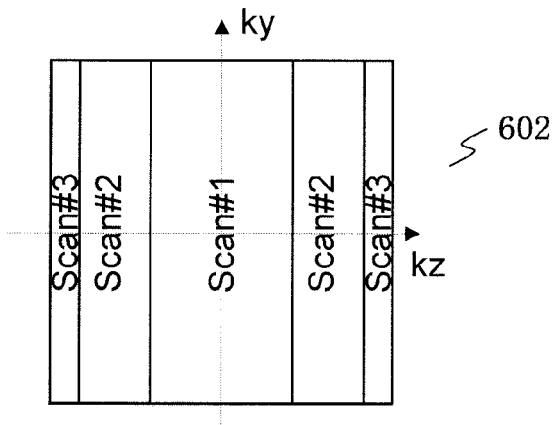
Figure 6:
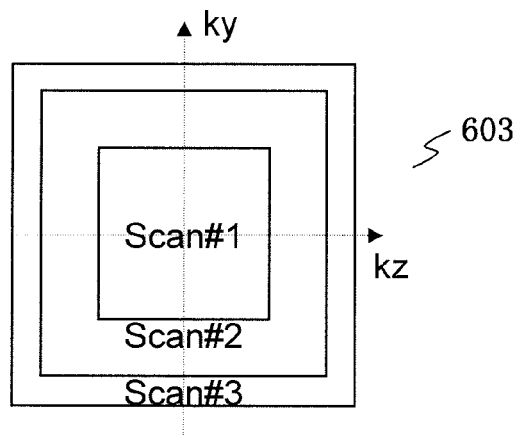

As examples of division in a ky (phase encoding direction)–kz (slice encoding direction) space at the time of three-dimensional measurement, three examples of (a) division only in the ky direction (601), (b) division only in the kz direction (602), and (c) division in the ky and kz directions (603) are shown in FIG. 6. In the case of dividing a three-dimensional k space in only one direction of 601 or 602, it is preferable that division is not performed in a direction, in which collection is performed first, of ky and kz and division is performed in a direction perpendicular thereto according to scan in the ky–kz space. The method of performing division in the ky and kz directions of 603 is useful when collecting the echo data at the center of the k space at early time in contrast test and the like. Moreover, although the k space is divided into rectangles in FIG. 6, it may also be divided into the shapes of concentric ellipses or the like from the k space center. In all of the division methods, the echo data is measured from the low-frequency region of the k space toward the high-frequency region in Scan #1 to Scan#3.

Figure 7:
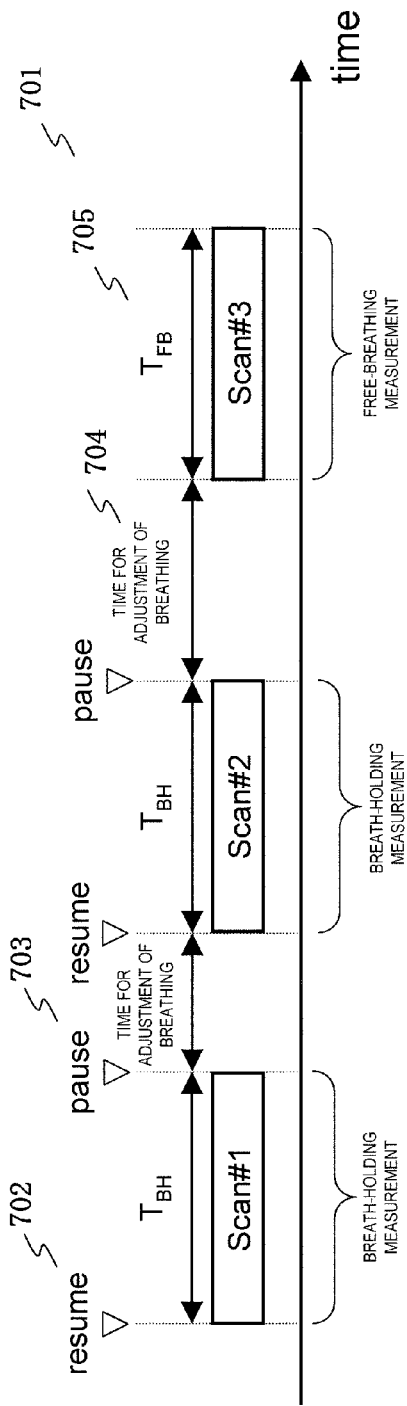
FIG. 7 is a view explaining a measurement method used in the present invention.
Figure 7:
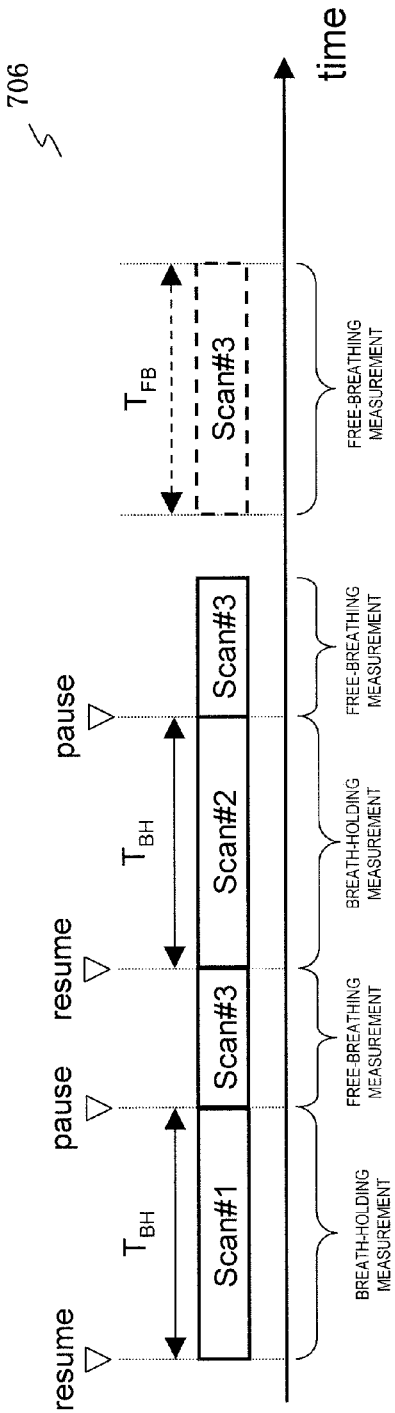

Hereinafter, details of the above-described divided breath-holding measurements in step 315 in three-dimensional measurement will be described using time charts (701 and 706) of FIG. 7. In FIG. 7, NBH=2 is assumed. Breath-holding measurement proceeds by repeating pause (703) and resumption (702) of the imaging sequence. An operator instructs a subject to stop breathing at the time of imaging pause 703 and resumes imaging 702. Therefore, a time from the pause of breathing to resumption is a time for adjustment of breathing of the subject. After resumption of imaging, breath-holding measurement is performed for TBH seconds. The sequence is stopped at the end, and the subject is instructed to stop breath holding. An instruction to start or stop breath holding may be given by the operator in the imaging room or may be given from the operation room through a microphone or the like. In addition, an automatic instruction voice or the like may be used.

First, an example where two breath-holding measurements are performed and then one free-breathing measurement is performed is shown in FIG. 7a (701). Since breathing is easily in a state of disorder immediately after the end of each breath-holding measurement, it is preferable to perform the next measurement after a time for adjustment of breathing (several seconds to tens of seconds) (704). After two breath-holding measurements end, free-breathing measurement is performed for TFB seconds (705). In addition, at the time of free-breathing measurement, stopping the sequence is not necessary.

Next, an example where free-breathing measurement is performed using a time for adjustment of breathing is shown in FIG. 7b (706). In the present embodiment, the execution order of each divided measurement does not matter. Accordingly, free-breathing measurement performed in 705 in FIG. 7a may also be performed during a time for adjustment of breathing after stopping of imaging as shown in FIG. 7b. In addition, echo data in each divided measurement is measured according to the arrangement set in step 313. Moreover, during the pause time, it is also possible to measure additional data, such as sensitivity distribution measurement data which is usually measured in pre-measurement or the like. However, in the case of measurement in which an acquisition time of a low-frequency region of the k space is decided in order to realize a desired contrast in a contrast test and the like, it may be better to match breath-holding measurement to the decided low-frequency region measurement time.

This is an explanation of the present embodiment. According to the MRI apparatus and the breath-holding imaging method of the present embodiment, a high-quality image can be acquired by setting the number of times of breath holding or a breath-holding time according to the subject, without the sacrifice of image quality or an increase in a burden on the subject caused by extension of an imaging time even in the case of imaging of a part with a body movement.

Second Embodiment

A second embodiment of the MRI apparatus and the breath-holding imaging method of the present invention will be described. In the first embodiment described above, TBH was set as a breath-holding time per time [second]. In the present embodiment, however, a total breath-holding time is included as imaging conditions for breath-holding measurement and TBH is set as a total time of "NBH" breath holding. That is, an upper limit of the burden in breath holding of the subject is set as the total breath-holding time TBH. Hereinafter, only a different point from the first embodiment will be described, and an explanation regarding the same point will be omitted.

Figure 8:
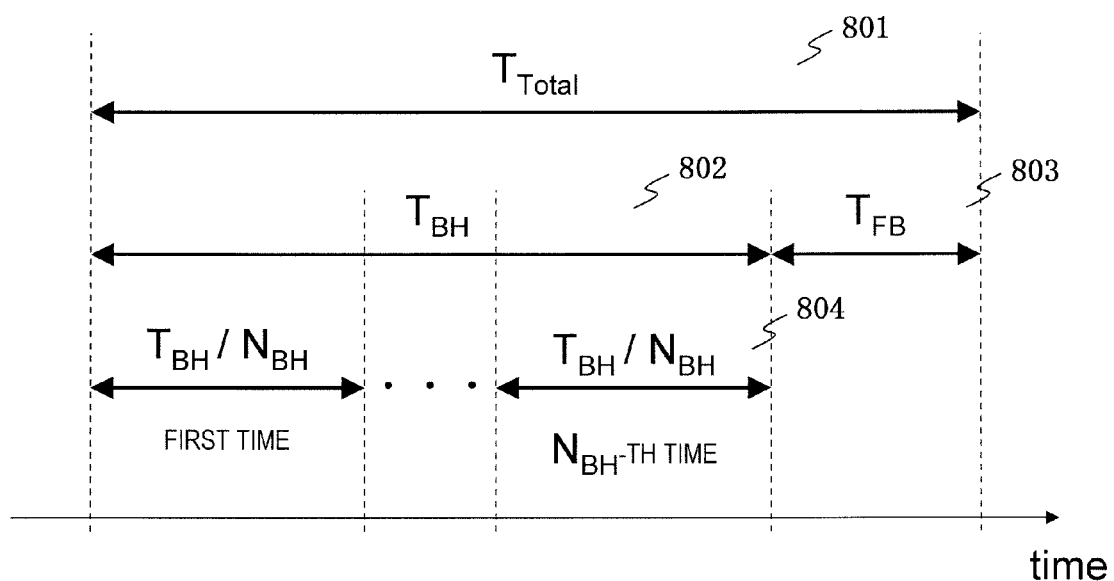
FIG. 8 is a view showing the processing concept of the present invention.
Figure 9:
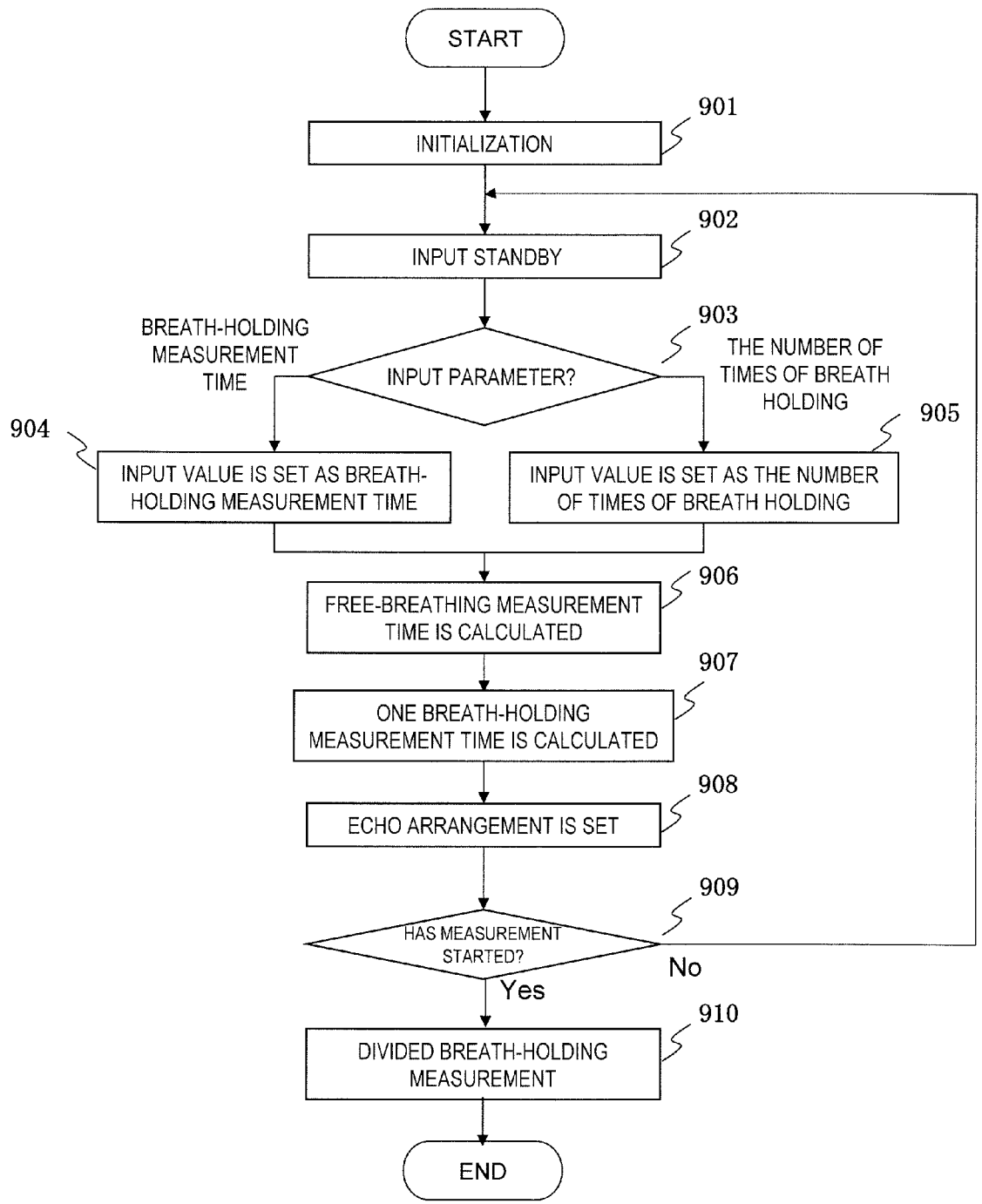
FIG. 9 is a view showing the process flow of the present invention.

FIG. 8 is a time chart showing the concept of the present embodiment, and FIG. 9 is a flow chart showing an example of the process flow of the present embodiment.

As shown in FIG. 8, in the present embodiment, first, a single scan with a total measurement time of TTotal [second] (801) is divided into a breath-holding measurement of TBH [second] (802) and a free-breathing measurement of TFB [second] (803). In addition, the breath-holding measurement of 802 is divided into breath-holding measurements (804) of the number of times of breath holding NBH.

Hereinafter, a specific operation of the present embodiment will be described by explaining the processing of each step of the flow chart shown in FIG. 9 in detail. In addition, this process flow is stored in an external storage device as a program and is executed when the CPU 8 reads it into the memory to execute it as necessary.

In step 901, first, the CPU 8 initializes each parameter by substituting the value into each parameter as shown in expression (2). In the initial state, it is normal breath-holding measurement in which a total measurement time is measured in one breath holding.

In step 902, the CPU 8 displays a GUI for setting of the parameters TBH and NBH on the display 20 so that input setting of the operator is possible and proceeds to an input standby state. As the GUI, those illustrated in FIG. 4 are used.

In step 903, the process is divided according to which parameter in TBH or NBH is input and set through the GUI in step 902. A different point from the first embodiment is that a parameter is not calculated automatically. That is, the value of a parameter input and set in step 903 is set as a value of the parameter as it is. Specifically, in step 904, if the breath-holding measurement time TBH is input and set, the CPU 8 substitutes the input value into TBH. In step 906, if the number of times of breath holding NBH is input and set, the CPU 8 substitutes the input value into NBH. In the present embodiment, these are to make it possible for an operator to set TBH and NBH independently.

$$TFB = TTotal - TBH \quad (14)$$

In step 906, the CPU 8 calculates a free-breathing time TFB on the basis of expression (14).

$$T_{PerBH} = \frac{T_{BH}}{N_{BH}} \quad (15)$$

In step 907, the CPU 8 calculates a measurement time per breath-holding measurement TperBH from expression (15).

In step 908, the CPU 8 sets the k space arrangement of echo data from TBH, and NBH and TFB set in steps 904 to 907, respectively, similar to step 313 in the first embodiment described above.

In step 909, an instruction to start measurement from the operator is waited. If there is an instruction, the process proceeds to step 910. In addition, in order to make it possible to repeatedly set each parameter described above until the measurement starts, the process proceeds to the above-described step 903 if one of the parameters is updated and input by the operator.

In step 910, the CPU 8 instructs the measurement controller 4 to start divided breath-holding measurements based on each parameter set as described above. In response to the instruction, the measurement controller 4 starts divided breath-holding imaging.

This is an explanation regarding an example of the process flow of the present embodiment. According to the MRI apparatus and the breath-holding imaging method of the present embodiment, the upper limit of the breath-holding burden on the subject can be set by setting the total breath-holding time as imaging conditions of breath-holding measurement. Accordingly, since the imaging conditions of breath-holding measurement are set within this upper limit, the burden on the subject can be further reduced.

Third Embodiment

A third embodiment of the MRI apparatus and the breath-holding imaging method of the present invention will be described. In each of the embodiments described above, there was no particular limitation on a pulse sequence. In the present embodiment, however, k space data is measured slice by slice when the present invention is applied to imaging using SSFP (Steady State Free Precession) sequence. Moreover, in breath-holding measurement, the low-frequency data of the k space corresponding to each slice is measured.

Figure 10:
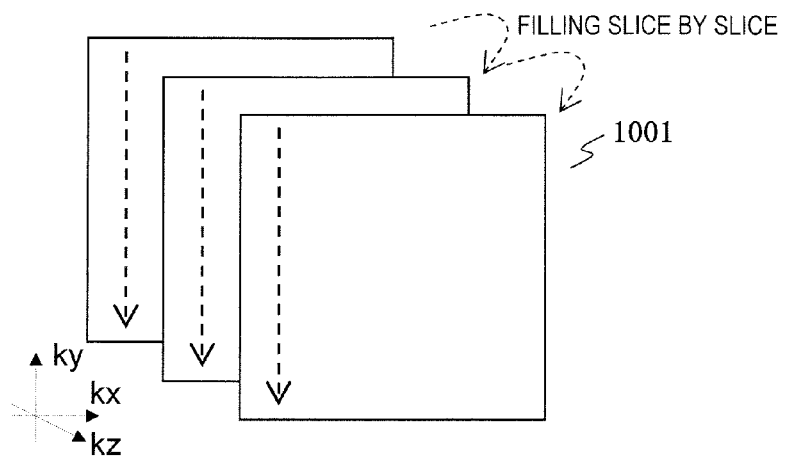
FIG. 10 is a view explaining a k space division method used in the present invention.
Figure 10:
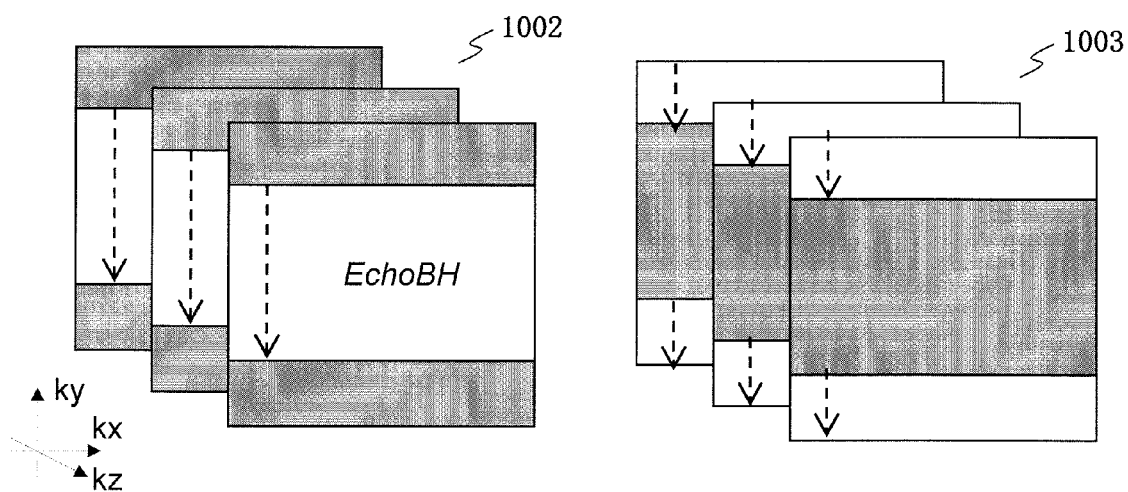

The SSFP sequence is a sequence in which an RF pulse is irradiated at short intervals (TR) and an echo signal is repeatedly measured from transverse magnetization shifted to the steady state (for example, JP-A-2004-329268. An example of filling the echo data into the k space in the SSFP sequence is shown in FIG. 10a. In the SSFP sequence, in many cases, the echo data is measured to fill the k space slice by slice so that the steady state of transverse magnetization does not collapse (1001). Hereinafter, only a different point from each of the above-described embodiments will be described, and an explanation regarding the same point will be omitted.

In the present embodiment in which the present invention is applied to the SSFP sequence, the echo data is filled by dividing the k space according to a breath-holding time TBH [second] and the number of times of breath holding NBH designated by the operator. The echo data measured during a breath-holding period of NBH times is filled in a low-frequency region of the k space, while the echo data measured during a free-breathing period is filled in a high-frequency region of the k space. Specifically, as shown in FIG. 10b, in a breath-holding period, the low-frequency echo data EchoBH including the center of the k space corresponding to one slice is measured. Then, a movement to the next slice is made to similarly measure the low-frequency echo data EchoBH including the center of the k space corresponding to the slice (1002). This is repeated while changing a slice in the breath-holding period. In the next breath-holding period, the low-frequency echo data EchoBH of the k space corresponding to a slice, which has not been yet measured, is measured. After repeating such breath-holding measurement NBH times, the echo data in a high-frequency region of the k space is measured in free-breathing measurement.

$$TDum = Dum\# \times TR \times MultiSlice \quad (16)$$

In one k space filling, the arrangement order of the echo data designated through the GUI is used in the same manner as in measurement in which the present invention is not applied. Here, in the SSFP sequence, when changing the slice position excited, a dummy sequence is necessary before the present measurement in order to make transverse magnetization in a steady state. When setting the arrangement of echo data, it is also necessary to consider a time spent for such a dummy sequence. Here, assuming that the dummy number necessary for one slice is Dum#, a repeat time is TR, and the number of slices acquired is MultiSlice, a time TDum which is spent in the dummy sequence and for which the echo data is not measured is expressed as expression (16).

$$EchoAll = \frac{T_{BH} - T_{Dum}}{TR} \quad (17)$$

Moreover, in the case of adding a pre-pulse to the SSFP sequence, segment measurement (for example, Japanese Patent No. 03283632) is used in which the k space is divided for measurement into a plurality of segments in a phase encoding direction. The segment measurement is a measurement in which the number of echo data measured after application of a pre-pulse is reduced to maintain the effect of the pre-pulse. For this reason, when the present invention is applied for the segment measurement using the SSFP sequence, it is necessary to consider a k space division number, that is, the number of segments. In consideration of the dummy sequence time TDum, the number of all echo data EchoAll which can be measured in the breath-holding time TBH is expressed as expression (17).

$$EchoBH = \frac{EchoAll}{MultiSlice} \quad (18)$$

If this is distributed to "MultiSlice" slices, the number of echo data EchoBH per slice measured in a breath-holding time can be expressed as expression (18).

$$Seg\# = \frac{EchoBH}{EchoSeg} \quad (19)$$

From EchoBH calculated in this way, the CPU 8 sets the k space arrangement of the echo data according to FIG. 5. In this case, assuming that the number of echo data measured per segment is EchoSeg, the segment repetition number Seg# can be expressed as expression (19).

Thus, one breath-holding measurement is divided into "Seg#" segment measurements. In addition, the segment measurement may be performed in the same manner as in normal measurement of the SSFP sequence.

In addition, the present embodiment may be combined with any of breath-holding setting described in the first and second embodiments described above.

As described above, according to the present embodiment, even in the case of multi-slice imaging for imaging of each slice using the SSFP sequence, the optimal breath-holding imaging conditions according to the subject can be set similar to the first and second embodiments described above. Therefore, a high-quality image can be acquired without the sacrifice of image quality or an increase in a burden on the subject caused by extension of an imaging time.

Fourth Embodiment

A fourth embodiment of the MRI apparatus and the breath-holding imaging method of the present invention will be described. In the third embodiment described above, the present invention was applied to the SSFP sequence. In the present embodiment, however, the present invention is applied to imaging using a multi-echo sequence, such as an FSE (Fast Spin Echo) sequence or an EPI (Echo Planar Imaging) sequence. The FSE or the EPI is a sequence in which a plurality of items of echo data are measured after one-time excitation using an RF pulse and the echo data is arrayed in one k space. Moreover, in the present embodiment, a region of the k space measured in breath-holding measurement is divided into segments, the number of which is the same as the number of echo data measured in one shot, for every echo data, the number of which is the same as the number of shots in one breath-holding period, and a plurality of items of echo data measured in one shot are arrayed in each segment. Hereinafter, only a different point from each of the above-described embodiments will be described, and an explanation regarding the same point will be omitted.

$$Phase = ShotNumber \times EchoFactor \qquad (20)$$

Generally, in imaging using a multi-echo sequence, echo numbers (#1, #2, ...) are given sequentially from echo data whose measurement time is close to an excitation RF pulse in order to distinguish a plurality of items of echo data measured. The contrast of an image obtained in such a sequence is determined by the echo number (effective TE: Echo Time) arrayed in the middle of the k space. Here, the number of times of excitation by an RF pulse for measuring the required number of echo data phase is called ShotNumber and the number of echo data measured per shot is called EchoFactor. These parameters have a relationship of expression (20).

Figure 11:
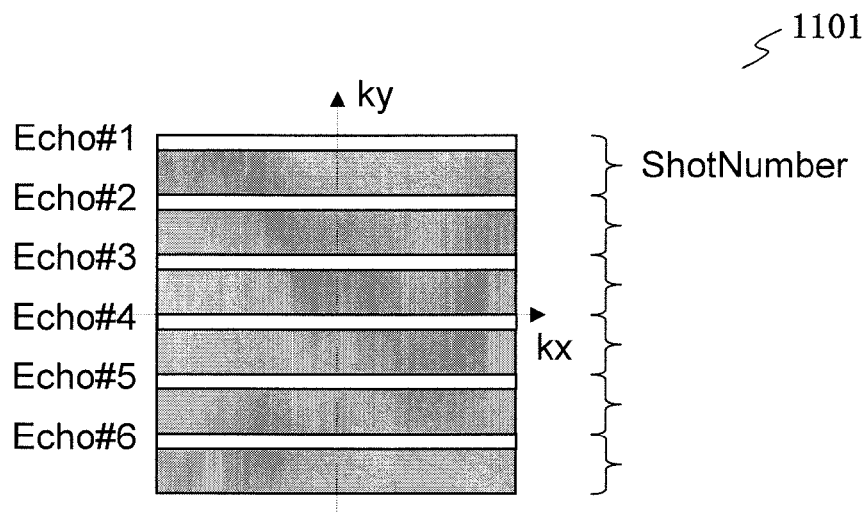
FIG. 11 is a view explaining a k space division method used in the present invention.
Figure 11:
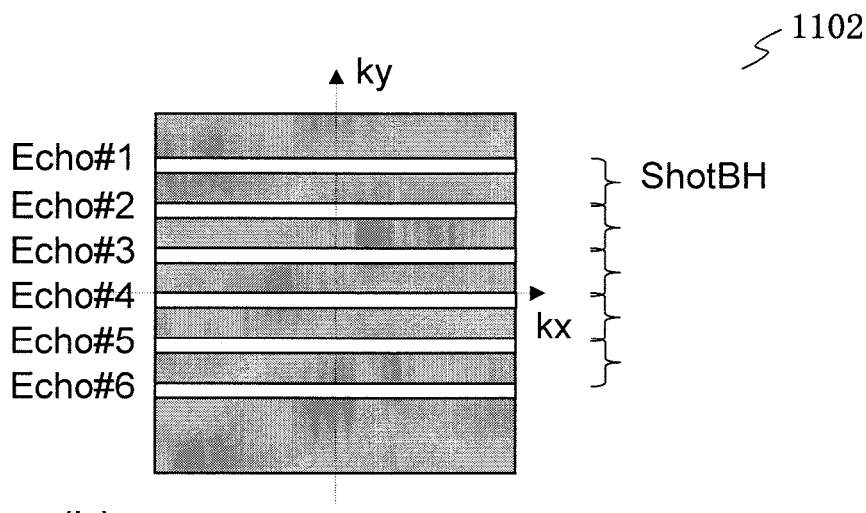

For example, an example of EchoFactor=6 and ShotNumber=4 is shown in FIG. 11. Since the measured echo data is filled in the k space for every echo number, a gap between the echo data measured in one shot becomes ShotNumber (1101).

$$ShotBH = \frac{T_{BH}}{TR} \text{ (round off anything below the decimal point)} \qquad (21)$$

In the case of the present embodiment where the present invention is applied to the EPI or FSE sequence, a minimum unit of the sequence is set as a shot and the echo number of echo data arrayed in the middle of the k space is not changed. The shot number ShotBH which can be measured in the breath-holding time TBH is expressed as expression (21) using the repetition time TR.

$$EchoBH = ShotBH \times EchoFactor \qquad (22)$$

That is, in echo data measurement, breath-holding measurement of ShotBH shots is repeated NBH times and then free-breathing measurement is performed. For this reason, an actual breath-holding time may be shorter than the set breath-holding time TBH. The number of echo data EchoEB which can be measured in breath-holding measurement can be expressed as expression (22).

The measured echo data is arrayed in the k space in the same order as the measured echo order such that the effective TE is not changed compared with that at the time of normal measurement. However, in order to array the echo data measured in breath-holding measurement in a low-frequency region of the k space, a gap between echo data is changed from the normal ShotNumber to ShotBH (1102). In the example of 1102, the echo data gap ShotBH is set to 3. Thereafter, free-breathing measurement is performed, such that the measured echo data is arrayed in a high-frequency region of the k space. Similar to the first embodiment, the order of encoding at the time of free-breathing measurement is preferably random so that motion artifacts caused by breathing movement are not imaged.

As described above, according to the present embodiment, even in the case of imaging using the multi-echo sequence, the optimal breath-holding imaging conditions according to the subject can be set similar to the first and second embodiments described above. Therefore, a high-quality image can be acquired without the sacrifice of image quality or an increase in a burden on the subject caused by extension of an imaging time.

Fifth Embodiment

A fifth embodiment of the MRI apparatus and the breath-holding imaging method of the present invention will be described. In each of the embodiments described above, each parameter is set for every scan. In the present embodiment, however, a type of scan in which imaging conditions of breath-holding measurement are applied can be selected and respective parameters are simultaneously set for the plurality of selected scans. Hereinafter, only a different point from each of the above-described embodiments will be described, and an explanation regarding the same point will be omitted.

Generally, a test protocol using an MRI apparatus includes a plurality of scans with different contrast. Hereinafter, the present embodiment will be described using FIGS. 12 and 13 regarding an example where divided breath-holding parameters are shared among total three scans of T1 stress imaging (T1W), T2 stress imaging (T2W), and T1 stress fat suppression imaging (T1WFS) in the abdomen test.

FIG. 12 is an example of a GUI for simultaneous setting of parameters related to the present embodiment. In FIG. 12a, a GUI for receiving an operator's selection of scans, parameters for which are to be simultaneously set, among a plurality of scans is shown (1201). For scans selected herein, parameters listed and set on the GUI shown in FIG. 12b are shared (1202). For scans not selected in 1201, they may be individually set.

Figure 13:
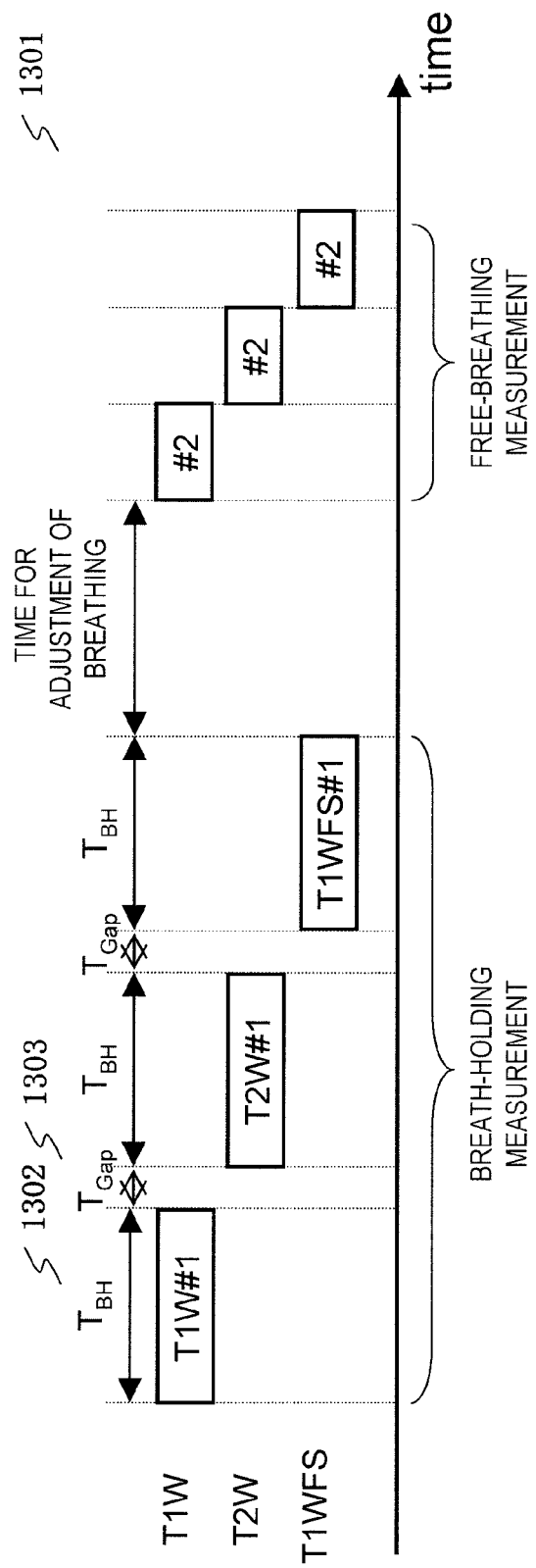
FIG. 13 is a view explaining a measurement method used in the present invention.

Parameters which can be simultaneously set are a breath-holding time TBH (1203) and the number of times of breath holding NBH (1204). In the case of simultaneous setting of parameters, it is preferable to set TBH directly because a measurement time differs with each scan. In addition, a time assigned to free-breathing measurement in each scan is different. FIG. 13 is an example of a time chart when parameters are simultaneously set (1301). In addition, although FIG. 13 shows the case of NBH=1, the same is true for the case of NBH>1. One breath-holding time is TBH (1302) which is the same in three scans. In addition, since a pause is included before each breath-holding measurement, TGAP becomes a value obtained by adding a time for adjustment of breathing and a pause time (1303). Although breath-holding measurements are collectively performed in the first half and free-breathing measurements are collectively performed in the second half in the example of 1301, such execution order is a random order.

In the present embodiment, in scans parameters for which are to be simultaneously set, two-dimensional measurement and three-dimensional measurement, different sequences, different imaging sections, and the like may be mixed. Specifically, the present invention may also be applied to the case where T1W is a two-dimensional GRE (gradient echo) sequence and T2W is a two-dimensional FSE sequence, and T1WFS is a three-dimensional fat suppression SSFP sequence.

As described above, according to the MRI apparatus and the breath-holding imaging method of the present embodiment, it is not necessary to set the breath-holding imaging conditions for every scan type. Accordingly, the operators burden in parameter setting can be reduced.

Sixth Embodiment

A sixth embodiment of the MRI apparatus and the breath-holding imaging method of the present invention will be described. In each of the embodiments described above, it is assumed that the subject maintains breath holding during the set breath-holding time TBH. In the present embodiment, however, when the subject stops breath holding before the set breath-holding time TBH ends, echo data which is not yet measured is measured in another breath-holding measurement or free-breathing measurement. Hereinafter, only a different point from each of the above-described embodiments will be described, and an explanation regarding the same point will be omitted. In addition, the present embodiment will be described on the basis of an example where one breath-holding measurement time is TBH and the number of times of breath-holding measurements NBH is set to 2.

In the present embodiment, it is determined whether or not the subject is in a breath-holding state from information including diaphragm navigation and a respiratory sensor. For example, if a residual error $|X_1-X_0|$ between the diaphragm detection position X1 and the previous detection position X0 is less than a predetermined value, it is determined that the subject is in a breath-holding state. In addition, the case is assumed that breath holding is stopped for certain reasons even though "EchoBH" echo data should be originally measured for TBH seconds of one breath-holding measurement. It is assumed that the number of echo data measured during a breath-holding period of n (1≤n≤NBH) times is EchoBH-$\alpha$n and "$\alpha$n" echo data is deficient compared with the set value EchoBH. In the present embodiment, it is assumed that the k space region, which was not filled through lack of echo data in the n-th breath-holding measurement, is filled in the (n+1)-th breath-holding measurement. Thus, "NBH" breath-holding measurements are repeated and "A" echo data which is deficient eventually is added to the free-breathing measurement and is measured.

$$-\frac{EchoBH}{2} \le ky \le \frac{EchoBH}{2} - 1 - \alpha_1 \quad (24)$$

$$\left(A = \sum_{n=1}^{N_{BH}} \alpha_n\right)$$

Figure 15:
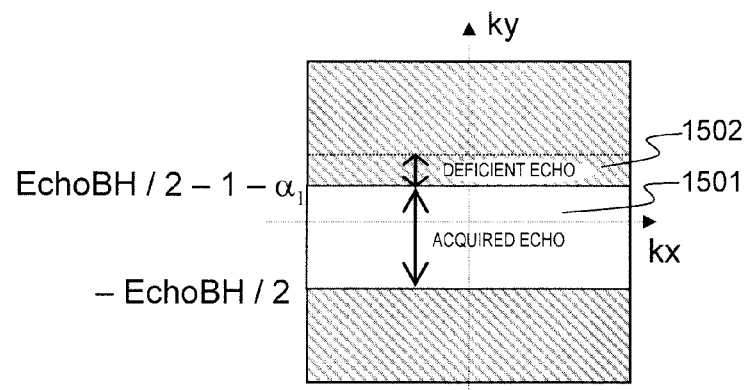
FIG. 15 is a view explaining a k space division method used in the present invention.
Figure 15:
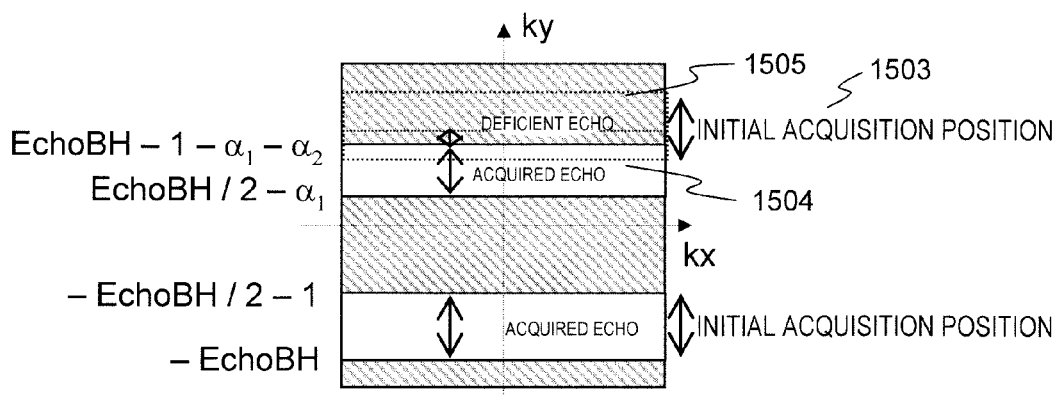
Figure 15:
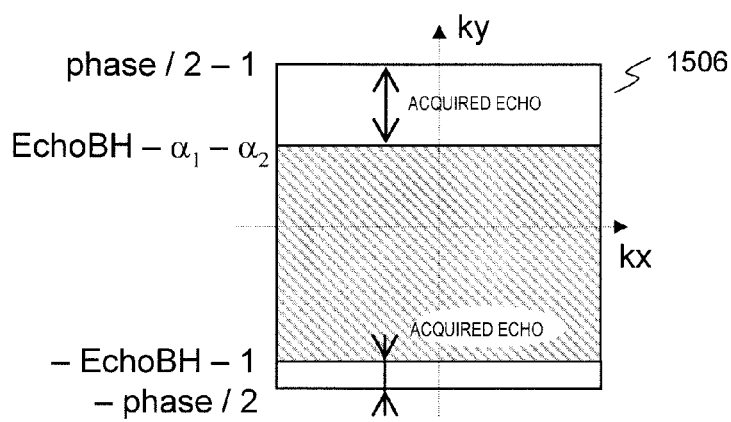

A specific example of the above-described processing is shown in FIG. 15. Two breath-holding measurements are defined as Scan #1 and Scan #2, and one free-breathing measurement is defined as Scan #3. Now, it is assumed that breath holding is stopped during the execution of Scan#1, the number of measured echo data (1501) is EchoBH-$\alpha$1, and "$\alpha$1" echo data is deficient (1502). That is, the phase encoding range measured in Scan#1 is expressed as expression (24) in the case of a sequential order.

$$-EchoBH \le ky \le -\frac{EchoBH}{2} - 1 \quad (25)$$

$$\frac{EchoBH}{2} - \alpha_1 \le ky \le EchoBH - 1 - \alpha_1 - \alpha$$

In the second breath-holding measurement Scan#2, the measured phase encoding range is set like expression (25) in order to compensate for a deficit $\alpha$1 in Scan#1, and the echo data is measured (1504) at the position shifted from the initial measurement position (1503). Expression (25) shows a state where breath holding is stopped in Scan#2 and the echo data is deficient (1505) by $\alpha$2. In addition, when deficiencies 1502 and 1505 do not occur in Scan#1 and Scan#2 ($\alpha$1=$\alpha$2=0), expression (25) becomes expression (11) to be the initial measurement position 1503.

$$-\frac{phase}{2} \le ky \le -EchoBH - 1 \quad (26)$$

$$EchoBH - \alpha_1 - \alpha_2 \le ky \le \frac{phase}{2} - 1$$

Finally, the phase encoding range measured in free-breathing measurement Scan#3 is expressed as expression (26). By performing free-breathing measurement by expression (26), the echo data, the number of which is larger by A (=$\alpha$1+$\alpha$2), deficient in Scan#1 and Scan#2 compared with expression (12) is measured (1506).

As described above, according to the present embodiment, even in the case where the subject stops breath holding and resumes breathing during breath-holding measurement, deficient echo data caused by stopping of breath holding is measured in another breath-holding measurement or free-breathing measurement. Therefore, even if there is unexpected stopping of breath holding, it becomes possible to acquire a high-quality image with no artifact based on breathing.

REFERENCE SIGNS LIST

1: subject
2: static magnetic field generating system
3: gradient magnetic field generating system
4: sequencer
5: signal transmission system
6: signal receiving system
7: signal processing system
8: central processing unit (CPU)
9: gradient magnetic field coil
10: gradient magnetic field power supply
11: high frequency oscillator
12: modulator
13: high frequency amplifier
14a: high-frequency coil (transmission coil)
14b: high-frequency coil (receiving coil)
15: signal amplifier
16: quadrature phase detector
17: A/D converter
18: magnetic disk
19: optical disk
20: display
21: ROM
22: RAM
23: track ball or mouse
24: keyboard
51: gantry
52: table
53: housing
54: processor

What is claimed is:
1. A magnetic resonance imaging apparatus comprising:
a measurement controller which acquires k space data by a breath-holding measurement to measure some data of the k space during a breath-holding period of a subject; and a breath-holding imaging condition input unit that receives an input of imaging conditions of the breath-holding measurement, wherein the measurement controller divides one scan into one or more breath-holding measurements and free-breathing measurements according to the imaging conditions including at least one of a breath-holding time and the number of times of breath-holding of the breath-holding measurement and controls a region of the k space measured in the breath-holding measurement.

2. The magnetic resonance imaging apparatus according to claim 1, wherein the measurement controller divides a low-frequency region of the k space according to the imaging conditions and measures data of each low-frequency region divided from the center of the k space toward a high-frequency region side in the breath-holding measurement.

3. The magnetic resonance imaging apparatus according to claim 1, wherein the imaging conditions of the breath-holding measurement include the number of times of breath holding.

4. The magnetic resonance imaging apparatus according to claim 1, wherein the imaging conditions of the breath-holding measurement include a ratio of the breath-holding time to a total imaging time.

5. The magnetic resonance imaging apparatus according to claim 1, wherein the measurement controller acquires some data of the k space even in the free-breathing measurement.

6. The magnetic resonance imaging apparatus according to claim 5, wherein the measurement controller acquires high-frequency data of the k space in the free-breathing measurement.

7. The magnetic resonance imaging apparatus according to claim 6, wherein the measurement controller measures data, which is measured in the free-breathing measurement, such that the data is arrayed at random on the k space.

8. The magnetic resonance imaging apparatus according to claim 1, wherein the imaging conditions of the breath-holding measurement include a parameter for adjusting a period of each breath holding.

9. The magnetic resonance imaging apparatus according to claim 1, wherein the imaging conditions of the breath-holding measurement include a total breath-holding time.

10. The magnetic resonance imaging apparatus according to claim 1, wherein when performing multi-slice imaging using an SSFP sequence, the measurement controller measures low-frequency data of the k space corresponding to each slice in the breath-holding measurement.

11. The magnetic resonance imaging apparatus according to claim 1, wherein when performing imaging using a multi-echo sequence, the measurement controller divides a region of the k space, which is measured in the breath-holding measurement, into segments, the number of which is the same as the number of echo data measured in one shot, for every echo data the number of which is the same as the number of shots in one breath-holding period and arrays a plurality of items of echo data measured in one shot in each segment.

12. The magnetic resonance imaging apparatus according to claim 1, wherein the breath-holding imaging condition input unit includes an input section which receives a selection of a scan type in which the imaging conditions of the breath-holding measurement are applied.

13. The magnetic resonance imaging apparatus according to claim 1, wherein the measurement controller measures echo data, which is not measured due to stopping of breath holding during the breath-holding measurement, in another breath-holding measurement or free-breathing measurement.

14. A breath-holding imaging method in a magnetic resonance imaging apparatus, the breath-holding imaging method comprising:
acquiring k space data by a breath-holding measurement to measure some data of the k space during the breath-holding period of a subject;
receiving an input of imaging conditions of the breath-holding measurement;
dividing one scan into one or more breath-holding measurements and free-breathing measurements according to the imaging conditions including at least one of a breath-holding time and the number of times of breath-holding of the breath-holding measurement; and
performing the breath-holding measurement by controlling a region of the k space measured in the breath-holding measurement.

15. The breath-holding imaging method according to claim 14, wherein a low-frequency region of the k space is divided according to the imaging conditions, and data of each low-frequency region divided is measured from the center of the k space toward a high-frequency side in the breath-holding measurement.

16. A magnetic resonance imaging apparatus comprising:
a measurement controller which acquires k space data by a breath-holding measurement to measure some data of the k space during a breath-holding period of a subject; and
a breath-holding imaging condition input unit that receives an input of imaging conditions of the breath-holding measurement,
wherein the measurement controller divides one scan into one or more breath-holding measurements and free-breathing according to a breath-holding time of the breath-holding measurement and controls a region of the k space measured in the breath-holding measurement.

17. The magnetic resonance imaging apparatus according to claim 16, wherein the measurement controller determines either the number of breath-holding or the breath-holding time based on each other.

\* \* \* \* \*